US010349885B2

(12) United States Patent
He et al.

(10) Patent No.: US 10,349,885 B2
(45) **Date of Patent: *Jul. 16, 2019**

(54) NON-INVASIVE BIOFEEDBACK SYSTEM

(71) Applicant: Wichita State University, Wichita, KS (US)

(72) Inventors: Jibo He, Wichita, KS (US); Jeremy Patterson, Wichita, KS (US)

(73) Assignee: Wichita State University, Wichita, KS (US)

(*) Notice: Subject to any disclaimer, the term of this patent is extended or adjusted under 35 U.S.C. 154(b) by 812 days.

This patent is subject to a terminal disclaimer.

(21) Appl. No.: 14/785,261

(22) PCT Filed: Jan. 16, 2014

(86) PCT No.: PCT/US2014/011880

§ 371 (c)(1),
(2) Date: Oct. 16, 2015

(87) PCT Pub. No.: WO2014/171983

PCT Pub. Date: Oct. 23, 2014

(65) Prior Publication Data

US 2016/0066835 A1 Mar. 10, 2016

Related U.S. Application Data

(60) Provisional application No. 61/813,500, filed on Apr. 18, 2013.

(51) Int. Cl.
*A61B 5/00* (2006.01)
*A61B 5/024* (2006.01)
(Continued)

(52) U.S. Cl.
CPC ............ *A61B 5/486* (2013.01); *A61B 5/0077* (2013.01); *A61B 5/024* (2013.01); *A61B 5/0205* (2013.01);
(Continued)

(58) Field of Classification Search
CPC ......... A61B 5/486; A61B 5/024; A61B 5/742; A61B 5/1032; A61B 5/6895;
(Continued)

(56) References Cited

U.S. PATENT DOCUMENTS 5,792,047 A 8/1998 Coggins
8,062,220 B2 11/2011 Kurtz et al.
(Continued)

FOREIGN PATENT DOCUMENTS

WO 2008142615 A2 11/2008

OTHER PUBLICATIONS

International Search Report and Written Opinion dated May 13, 2014, in Corresponding PCT/US2014/011880 (13 pages).
(Continued)

*Primary Examiner* — Sundhara M Ganesan
(74) *Attorney, Agent, or Firm* — Hovey Williams LLP

(57) ABSTRACT

A method, system, and computer program for non-invasively monitoring a physiological parameter and providing biofeedback. The method, system, and computer program provide for the non-invasive detection of a physiological parameter by detecting changes in color channel values of a user in a live video feed and presenting biofeedback to the user indicating the relative position of the physiological parameter to an optimal range.

35 Claims, 5 Drawing Sheets

400
410
420
430
440
450
460
470
90bpm
Intensity

(51) Int. Cl.
*A61B 5/103* (2006.01)
*A61B 5/145* (2006.01)
*A61B 5/0205* (2006.01)
*A63B 24/00* (2006.01)
*A63B 71/06* (2006.01)

(52) U.S. Cl.
CPC ........ *A61B 5/02438* (2013.01); *A61B 5/1032* (2013.01); *A61B 5/14542* (2013.01); *A61B 5/14546* (2013.01); *A61B 5/6895* (2013.01); *A61B 5/6897* (2013.01); *A61B 5/6898* (2013.01); *A61B 5/7257* (2013.01); *A61B 5/742* (2013.01); *A63B 24/0062* (2013.01); *A63B 24/0075* (2013.01); *A63B 24/0087* (2013.01); *A63B 71/0619* (2013.01); *A61B 2503/10* (2013.01); *A63B 2024/0065* (2013.01); *A63B 2024/0068* (2013.01); *A63B 2220/806* (2013.01); *A63B 2230/06* (2013.01)

(58) Field of Classification Search
CPC . A61B 5/7257; A61B 5/6897; A61B 5/02438; A61B 5/0077; A61B 5/6898; A61B 2503/10; A63B 24/0087; A63B 24/0075
See application file for complete search history.

(56) References Cited

U.S. PATENT DOCUMENTS

| | | | | |
|---|---|---|---|---|
| 8,321,004 | B2 | 11/2012 | Moon et al. | |
| 8,328,420 | B2 | 12/2012 | Abreu | |
| 2006/0084551 | A1 | 4/2006 | Volpe, Jr. | |
| 2006/0240947 | A1* | 10/2006 | Qu ..................... | A63B 24/0084 482/1 |
| 2008/0194928 | A1 | 8/2008 | Bandic et al. | |
| 2009/0203998 | A1 | 8/2009 | Klinghult et al. | |
| 2009/0226071 | A1 | 9/2009 | Schuler et al. | |
| 2009/0245603 | A1 | 10/2009 | Koruga et al. | |
| 2010/0185064 | A1 | 7/2010 | Bandic et al. | |
| 2011/0251493 | A1 | 10/2011 | Poh et al. | |
| 2013/0079649 | A1 | 3/2013 | Mestha et al. | |
| 2013/0095459 | A1 | 4/2013 | Tran | |
| 2013/0215042 | A1 | 8/2013 | Messerschmidt et al. | |

OTHER PUBLICATIONS

Kwon et al, "Validation of heart rate extraction using video imaging on a built-in camera system of a smartphone", available online 2012, available at: http://abrc.snu.ac.kr/sjkwon/EMBC2012.pdf (4 pages).

Liu et al., A review of non-contact, low-cost physiological information measurement based on photoplethysmographic imaging, available online 2012. 2012, The Institution of Engineering and Technology (2 pages).

Morales, Facial segmentation using the Active Shape Model for the contactless monitoring of vital signals, available online 2013, available at: http://upcommons.upc.edu/pfc/bitstream/2099.1/16983/4/ASM_segmentation_rPPG.pdf (80 pages).

Garbey et al., Contact-free measurement of cardiac pulse based on the analysis of thermal imagery, Department of Computer Science, University of Houston, Houston, Texas, Technical Report No. UH-CS-04-08, Dec. 14, 2004, available online 2007, available at: http://citeseerx.ist.psu.edu/viewdoc/download?doi=10.1.1.130.1981&rep=rep1&type=pdf (14 pages).

Ji et al., Real-Time Eye, Gaze, and Face Pose Tracking for Monitoring Driver Vigilance., Real-Time Imaging 8, 357-377 (2002), 2002 Elsevier Science Ltd., available online 2002, available at: http://www.ecse.rpi.edu/~qji/rti.pdf (21 pages).

Lee et al., Implementation of Face Tracking System for Noncontact Respiration Monitoring, 2012 International Conference on Future Information Technology and Management Science & Engineering Lecture Notes in Information Technology, vol. 14, available online 2012, available at http://www.ier-institute.org/2070-1918/Init14/v14/160.pdf (4 pages).

* cited by examiner 500
510
520
530
540
550
560
560
570
580
590
90bpm
Intensity

NON-INVASIVE BIOFEEDBACK SYSTEM

CROSS-REFERENCE TO RELATED APPLICATIONS

The present application is the National Stage of International Patent Application No. PCT/US2014/011880, filed Jan. 16, 2014, entitled NON-INVASIVE BIOFEEDBACK SYSTEM, which is hereby incorporated by reference in its entirety, and which claims the priority benefit of U.S. Provisional Patent Application Ser. No. 61/813,500, filed Apr. 18, 2013, entitled "MOBILE BIOFEEDBACK SYSTEM," incorporated by reference in its entirety herein.

BACKGROUND

Field of the Invention

Embodiments of the invention are directed to a non-invasive biofeedback system. More particularly, embodiments of the invention are directed to providing a new system, method, and computer program for using a computing device with an optical input device, such as a webcam or mobile phone camera, for non-invasively monitoring a physiological parameter of a user and providing biofeedback to the user based on physiological responses to physical activity.

Description of Related Art

Cardiotocography, the measurement of heart rate, is a critical indicator of physiological health and has wide reaching applications in the medical field. A human's heart rate alone is the independent risk predictor of cardiovascular disease and is also one of the most frequently used measurements to monitor operator workload and fatigue.

Traditionally, electrocardiographs (ECG) or pulse rates have been used to measure a heart rate. Heart rates are most accurately measured with an electrocardiograph, which records the electrical activity of the heart over a period of time. Commercial heart-rate monitoring devices often include a chest strap with heart-rate monitoring electrodes and a display (or a receiver such as a watch) for displaying the gathered data. In the alternative, one can measure heart rate by taking the pulse rate, by palpating an artery and counting pulse over a given period of time (beats/minute). Traditional measurements of heart rate often require the physically invasive attachment of disposable electrodes on the skin. Traditional devices are not only inconvenient, but also have the potential of spreading disease.

Considering the constant increases of medical costs in developed countries and the lack of trained healthcare personnel in less-developed countries, a need is presented for a more convenient and affordable solution to measure heart rate. One of these needs may be solved by the implementation of cardiotocographical functionality on a general computing platform, such as a personal computing device. It is known in the relevant art that light reflections off a human face changes as blood palpitates throughout the face, thereby causing rhythmic changes in the color space (e.g., "RGB" (red, green, and blue) pixel values, HSV (Hue, Saturation and Value) pixel values) detected by a camera. With the right software, a computer and a camera in communication with the computer are capable of detecting these changes in the color space for stationary subjects. However, accuracy and functionality have been limited by current developments.

Computers are generally available in the majority of households and/or medical facilities. The implementation of cardiotocographical functionality on a general computing platform can provide great benefits to a wide array of health-related applications. Further, mobile platforms such as cell phones, now have comparable processing power to desktop computers and can make for very portable solutions.

Compared to the traditional approach, mobile cardiotocography has the advantage of ubiquitous and easy data logging, along with portability. Users with smartphones often carry their phones around for most of their daily activities—this provides for the potential of assessing a user's heart rate at any given moment. For example, large populations of users carry their cellphones while exercising to stay connected and to listen to music. While modern exercise machines have made attempts at measuring a user's heart rate using electrodes built into machine handles or utilizing wearable monitors like chest straps or finger probes, such monitors are unpopular due to their invasive nature, the constant interruptions required for measurement during an exercise regimen, and the likelihood of spreading unwanted germs. Nevertheless, there are great benefits of heart rate monitors being used with exercise machines. For example, biofeedback provided to a user undergoing an exercise routine can provide the user with signals as to their ideal range of heart rate and the optimal intensity for maximizing results of an exercise regimen. Biofeedback, however, is most beneficial when a constant measurement is tracked and used for adjusting intensity as needed in real-time.

Modern technology, specifically mobile devices, has revolutionized the way users keep track of their personal data and share such data to the world. Fitness routines and results, for example, are one of the many data points users like to keep personal records for and share to their social media audience. A commonly perceived downside of modern exercise machines is the lack of personalized record keeping. Generally, if a first user utilizes machine-incorporated biofeedback technology, their exercise regimen and biofeedback records remain on the machine and records are ultimately deleted upon the commencement of a second user's exercise routine. Computing devices, on the other hand, have the convenience of data storage in either the device memory or on a remote server.

Accordingly, there is a need for a non-invasive and portable approach to cardiotocography that provides a user the convenience and accuracy of real-time biofeedback, the ability to optimize exercise regimens based on calculated factors incorporating the real-time biofeedback data, and the ability to keep a personal and/or mobile record of the data over a period of time for the calculation of a collective, long-term biofeedback.

SUMMARY

The invention provides for a method, system, and computer program for non-invasively measuring a non-stationary user's heart rate and providing biofeedback. More particularly, the invention provides for a method, system, and computer program for using a computing device with an optical camera for non-invasively measuring physiological parameters of a user during exercise and providing biofeedback to the user based on such measurements. In another embodiment, the invention is operable to non-invasively determine the user's heart rate, process the associated data with user-specific factors, and send data to a user's exercise machine operable to modify the intensity in real-time for achieving optimization of the user's exercise regimen. Even further embodiments of the invention are operable to collect records of the data over a period of time to calculate a collective, long-term biofeedback.

When determining a user's heart rate, embodiments of the invention utilize a computing device and a camera operably in communication with the computing device. The invention utilizes a computing device and a camera operably in communication with the computing device for optically observing a user, detecting changes in color channel values of the user's facial pixels, running signal processing algorithms on the live data feed, and producing an accurate measurement of heart rate.

Embodiments may further determine, based on a user's heart rate at a particular moment in time, a biofeedback for display to the user. The biofeedback may be operable to inform the user if they are below or above their anaerobic threshold, typically determined by analyzing the user's current heart rate and comparing said current heart rate to the user's heart rate training zone. Heart rate training zones are generally known in the art to be calculated with a user's maximum heart rate, resting heart rate, and age, or more accurately by performing cardio assessments for determination thereof. The invention may involve a computer program for receiving and storing the user's training zone data, or receiving and storing data associated to the detected physiological parameter, and utilizing such data to perform cardio assessments determining the user's training zones. The invention may further provide the user with biofeedback during exercise, and provide real-time instructions to the user or exercise machine for enabling the user's optimal aerobic intensity. Finally, the invention may provide the user with biofeedback in a post-workout, non-monitoring state, such that a biofeedback is calculated based on a collective record of data over a period of time for the purpose of advising the user on how to further optimize their exercise routine.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWINGS

Embodiments of the invention are described in detail below with reference to the attached drawing figures, wherein.

Figure 1:
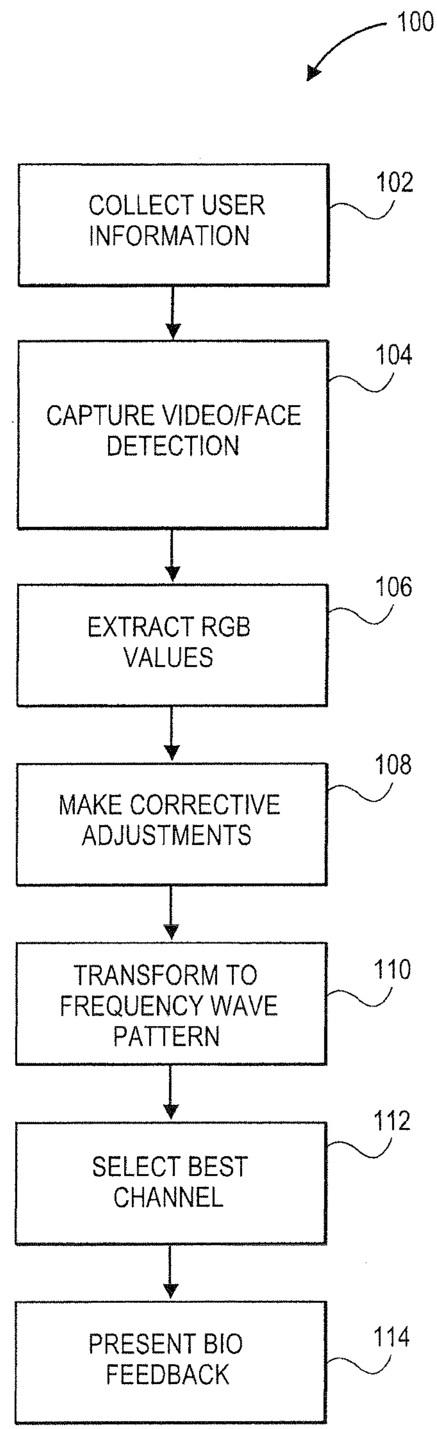
FIG. 1 is a flow chart of a method of non-invasively detecting a physiological parameter and using said parameter for providing biofeedback.

The drawing figures do not limit the invention to the specific embodiments disclosed and described herein. The drawings are not necessarily to scale, emphasis instead being placed upon clearly illustrating the principles of the invention.

DETAILED DESCRIPTION OF PREFERRED EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

Embodiments of the invention are directed to a computer program, method, and system for the non-invasive detection of physiological parameters of a user performing a physical activity, displaying the physiological parameters to the user, and further providing biofeedback for altering exercise intensity to meet optimal aerobic intensities specific to the user's aerobic training zones. The term "biofeedback" refers to the provision of a user's physiological parameters (e.g., heart rate, respiration rate, etc.) to the user for facilitating the training and control of the physiological parameter. The term "optimal" or "optimal range," as used herein refers to the preferred range of a user's physiological parameters (e.g., heart rate), such that the preferred range is equivalent to an aerobic training zone best suited for achieving the user's desired fitness goals. For example, fitness goals such as weight loss, physical therapy, long distance cardiovascular fitness, sprint training, aerobic/anaerobic fitness, etc., are all non-limiting examples of a user's desired fitness goals and may require training within a variety of different aerobic training zones over a varying duration of time. The term "training zones" as used herein describes a minimum and maximum value of a physiological parameter, wherein the minimum and maximum value set a recommended range for a particular user. Details for determining a user's training zones are described further herein. It is within the scope of this invention that a user may have a plurality of different optimal ranges for achieving a plurality of different fitness goals. A user may utilize embodiments of the invention for "optimizing" their exercise regimen, such that the biofeedback features facilitate the user's current exercise to reach those goals more efficiently or effectively. The optimal or optimized range that is preferred may be set by the user himself, or may be set according to an objectively-designated range according to known training zone ranges for a desired fitness goal. In either case, this optimal range can be used to "optimize" the user's exercise routine.

The computer program of embodiments of the invention comprises a plurality of code segments executable by a computing device for performing the steps of the method of the invention. The steps of the method may be performed in the order shown in FIG. 1, or they may be performed in a different order, unless otherwise expressly stated. Furthermore, some steps may be performed concurrently as opposed to sequentially. Also, some steps may be optional or substituted.

The user of the invention may selectively activate a program mode for desired operational features. The invention includes at least two program modes, namely a monitoring mode and a biofeedback mode. In further embodiments of the invention, a third program mode, referred to as an exercise machine control mode, may also be activated by the user. In all modes, with the exception of an off mode, the functions of a monitoring mode are necessarily activated.

The computer program and method of embodiments of the invention comprise the steps 100 of detecting a physiological parameter of a user by (1) collecting user information 102; (2) tracking a facial area of a subject in a live video feed 104; (3) detecting a first set of at least two channel values from the facial area of the subject in each frame of the live video feed 106; (4) performing a function to make corrective adjustments for subject motion and changes in lighting conditions on the first set of the at least two channel values, wherein the results of the function produce a second set of at least two channel values corresponding to the first set of at least two channel values, such that a total of at least four channel values are associated to each frame of the live video feed 108; (5) transforming the channel values into a frequency wave pattern 110; (6) selecting a single channel amongst the at least four channel values, wherein said single channel provides the strongest indicia for physiological parameter detection 112; (7) presenting a biofeedback to the user on a display 114. As used herein, the phrase "channel values" refers to the reference values used for describing color. Color reference values are generally comprised of an array of values used to describe a specific color in a well-known color space (e.g., RGB, HSV, or HSL) as further described herein.

The system of embodiments of the invention may comprise computing devices, servers, and communications networks to facilitate the functions and features described herein. The computing devices and servers may comprise any number and combination of processors, controllers, integrated circuits, programmable logic devices, or other data and signal processing devices for carrying out the functions described herein, and may additionally comprise one or more memory storage devices, transmitters, receivers, and/or communication busses for communicating with the various devices of the system. In various embodiments of the invention, the computing devices may comprise a memory element, a communication component, a display, and/or a user interface.

Figure 2:
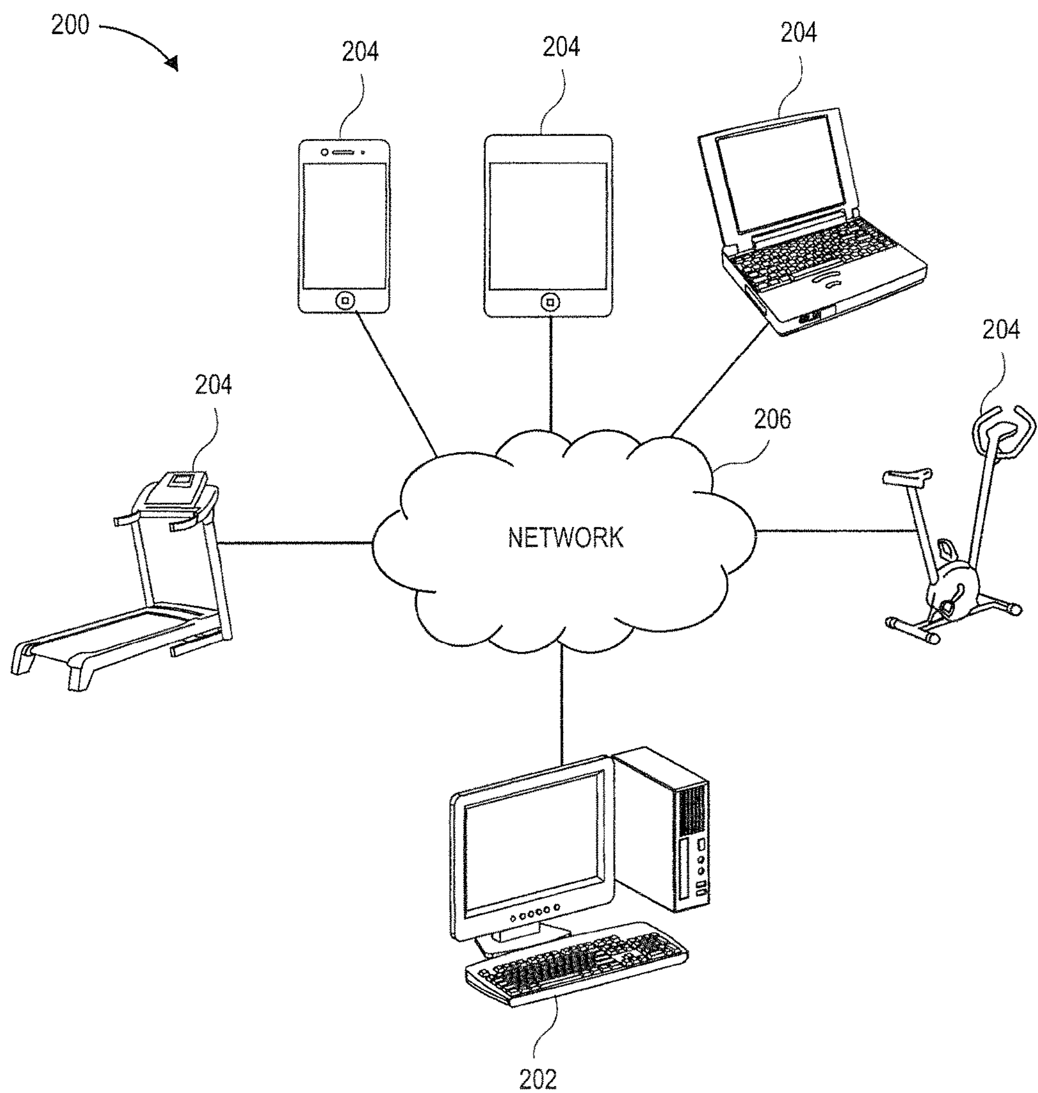
FIG. 2 is a functional block diagram of an exemplary operating environment in which an embodiment of the invention can be implemented.

The computer program, system, and method of embodiments of the invention may be implemented in hardware, software, firmware, or combinations thereof using system 200, shown in FIG. 2, which broadly comprises server devices 202, computing devices 204, and a communications network 206. The server devices 202 may include computing devices that provide access to one or more general computing resources, such as Internet services, electronic mail services, and data transfer services, and the like.

The server devices 202 and computing devices 204 may include any device, component, or equipment with a processing element and associated memory elements. The processing element may implement operating systems, and may be capable of executing the computer program, which is also generally known as instructions, commands, software code, executables, applications, apps, and the like. The processing element may include processors, microprocessors, microcontrollers, field programmable gate arrays, and the like, or combinations thereof. The memory elements may be capable of storing or retaining the computer program and may also store data, typically binary data, including text, databases, graphics, audio, video, combinations thereof, and the like. The memory elements may also be known as a "computer-readable storage medium" and may include random access memory (RAM), read only memory (ROM), flash drive memory, floppy disks, hard disk drives, optical storage media such as compact discs (CDs or CDROMs), digital video disc (DVD), Blu-Ray™, and the like, or combinations thereof. In addition to these memory elements, the server devices 202 may further include file stores comprising a plurality of hard disk drives, network attached storage, or a separate storage network.

The computing devices 204 may specifically include mobile communication devices (including wireless devices), work stations, desktop computers 204, laptop computers 204, palmtop computers, tablet computers 204, portable digital assistants (PDA), smart phones 204, scanners, exercise machine computers 204, cash registers, cash drawers, printers, and the like, or combinations thereof. Various embodiments of the computing device 204 may also include voice communication devices, such as cell phones 204 or landline phones. In preferred embodiments, the computing device 204 will have an electronic display, such as a cathode ray tube, liquid crystal display, plasma, or touch screen that is operable to display visual graphics, images, text, etc. In certain embodiments, the computer program of the invention facilitates interaction and communication through a graphical user interface (GUI) that is displayed via the electronic display. The GUI enables users (e.g., the consumer, an athlete, an exercise enthusiast, or an administrator) to interact with the electronic display by touching or pointing at display areas to provide information to the user control interface. In additional embodiments, the computing device 204 may include an optical device such as a digital camera, video camera, webcam, infrared scanner, optical scanner, or the like, such that the computing device can capture, store, and transmit digital images and/or videos. Any and all components may be directly in communication with a computing device, or wirelessly connected to a computing device through a communications network.

The computing devices 204 may include a user control interface that enables one or more users to share information and commands with the computing devices or server devices 202. The user interface may comprise one or more functionable inputs such as buttons, keyboard, switches, scrolls wheels, voice recognition elements such as a microphone, and pointing devices such as mice, touchpads, tracking balls, and styluses. The user control interface may also include a speaker for providing audible instructions and feedback. Further, the user control interface may comprise wired or wireless data transfer elements, such as a communication component, removable memory, data transceivers, and/or transmitters, to enable the user and/or other computing devices to remotely interface with the computing device 204.

The communications network 206 may be wired or wireless and may include servers, routers, switches, wireless receivers and transmitters, and the like, as well as electrically conductive cables or optical cables. The communications network 206 may also include local, metro, or wide area networks, as well as the Internet, or other cloud networks. Furthermore, the communications network 206 may include cellular or mobile phone networks, as well as landline phone networks, public switched telephone networks, fiber optic networks, or the like. The network may be the Internet, an intranet, or a telecommunications network. The server device may be any derivation of the computing device, operable to store and host data. The server device is operable to accept data packets from a computing device via a communications network, such as the Internet, a Wi-Fi link, Bluetooth, Near-Field Communications ("NFC"), a radio-frequency ("RF") link, or directly via a manual connection, such as a universal serial bus ("USB"), and Ethernet port.

Both the server devices 202 and the computing devices 204 may be connected to the communications network 206. Server devices 202 may be able to communicate with other server devices 202 or computing devices 204 through the communications network 206. Likewise, computing devices 204 may be able to communicate with other computing devices 204 or server devices 202 through the communications network 206. The connection to the communications network 206 may be wired or wireless. Thus, the server devices 202 and the computing devices 204 may include the appropriate components to establish a wired or a wireless connection. In some embodiments, the server device and the computing device may be the same computing device, wherein the computing device servers all functions of the server device.

The computer program of the invention may run on computing devices 204 or, alternatively, may run on one or more server devices 202. Thus, a first portion of the program, code, or instructions may execute on a first server device 202 or a first computing device 204, while a second portion of the program, code, or instructions may execute on a second server device 202 or a second computing device 204. In some embodiments, other portions of the program, code, or instructions may execute on other server devices 202 as well. In additional embodiments of the invention, a portion of the information to implement the invention may be stored on the server device 202, while another portion may be stored on the one or more computing devices 204. The various processes described herein as being performed by or using the computer program may actually be performed by one or more computers, processors, or other computational devices, such as the computing devices 204 and/or server devices 202, independently or cooperatively executing portions of the computer program.

In certain embodiments of the invention, the computer program may be embodied in a stand-alone program downloaded on a user's computing device 204 or in a web-accessible program that is accessible by the user's computing device 204 via the network 206. For the stand-alone program, a downloadable version of the computer program may be stored, at least in part, on the server device 202. A user can download at least a portion of the computer program onto the computing device 204 via the network 206. In such embodiments of the invention, the computer program may be an "application," such as an "app" for a mobile device. After the computer program has been downloaded, the program can be installed on the computing device 204 in an executable format. The executable form of the program permits the user to access embodiments of the invention via an electronic resource, such as a mobile "app" or website. For the web-accessible computer program, the user may simply access the computer program via the network 206 (e.g., the Internet) with the computing device 204.

Figure 3:
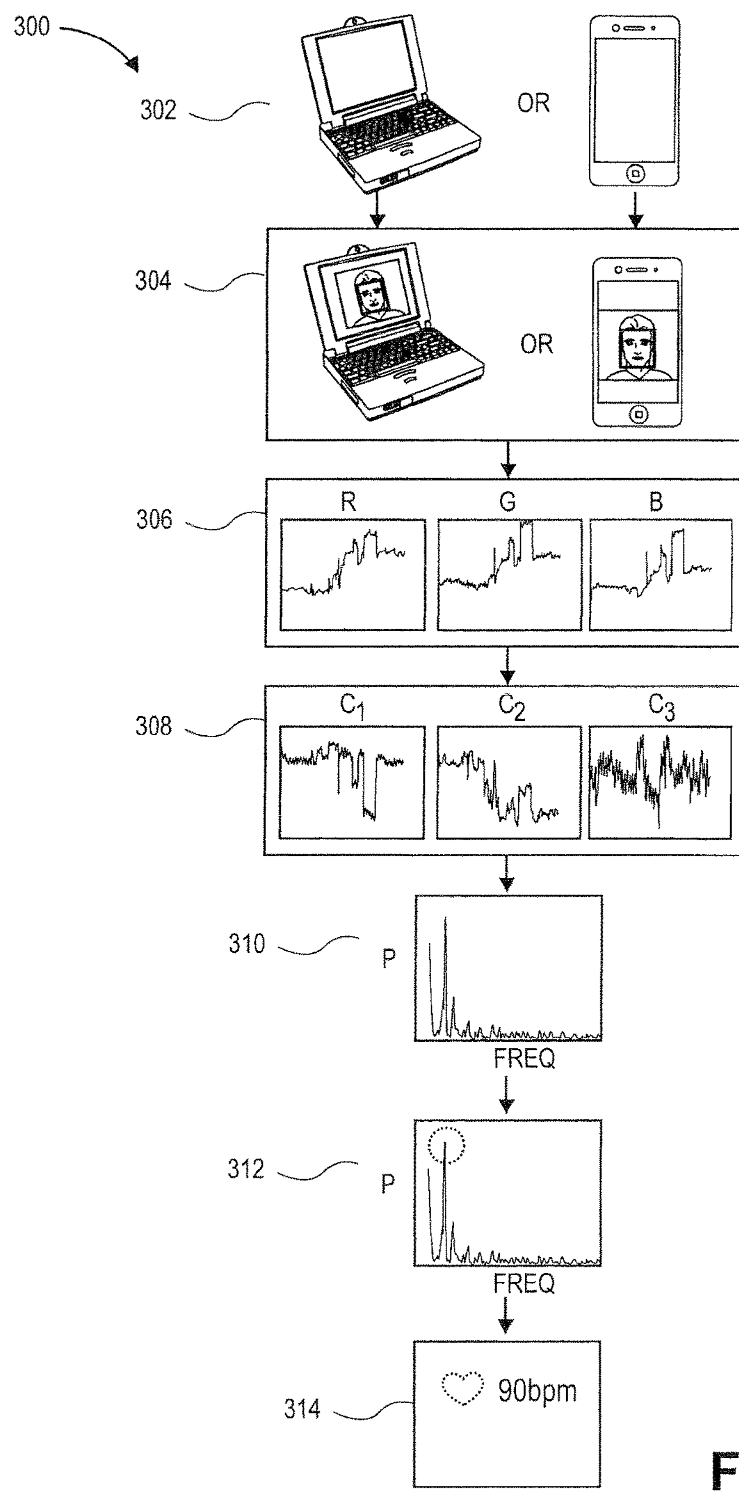
FIG. 3 is a flow diagram of an exemplary process flow of embodiments of the invention.

The invention detects physiological parameters of a user stationary or in motion, as described in the steps of FIGS. 1 & 3. In a monitoring mode, the invention provides for the non-invasive detection of the physical parameter utilizing a camera and an operably connected computing device, specifically, the detection and calculation of a user's heart rate 300. Additional physiological parameters such as respiration rate, blood concentration, heart rate variability, oxygen saturation, lactate levels, aerobic capacity, anaerobic capacity, posture, pallor, perspiration levels, and running speed, may be detected and/or calculated using same or similar concepts or principles as disclosed in the invention. It is within the scope of this invention that such other physiological parameters may be used in conjunction with the detection of a user's heart rate to provide more accurate and in-depth biofeedback analysis to the user. Biofeedback analysis corresponding to a user's heart rate requires at least the collection of some basic information about the user 302, as further described below in the biofeedback description. The invention is concerned with detecting the user's heart rate while the user is stationary or performing a physical act (e.g., running on a treadmill). The system embodiment of the invention is comprised of a camera operably in communication with a computing device 302, wherein the camera is operable to stream a live video feed to the computing device for processing 304. Speed of results is important in this invention, therefore embodiments may resize the resolution of the video frames to speed up processing. As the computing device receives the live video feed from the camera, the computer program and the method of embodiments of the invention utilize computer vision algorithms for detecting facial areas 304. As used herein, "facial areas" refers to the forward-facing view of a user's face, such that at least the user's eyes, nose, and mouth are visible to the camera. Facial area tracking utilizes known facial detection methods such as skin-color detection or Haar-like feature detection. It is within the scope of the invention to utilize skin-color detection for embodiments that track a user's body parts other than their "facial areas," as typically tracked using Haar-like feature detection. Embodiments of the computing device receive frames streamed from the video feed captured by the camera, and extract color arrays 306 from the facial area and perform an independent component analysis (ICA) to each array from at least two of three color channels to correct for user head motion and changes in lighting conditions 308, resulting in a total of at least four color arrays. The color channels are generally extracted according to RGB (Red, Green, and Blue) color space 306, however, HSV (Hue, Saturation, and Value) and/or HSL (Hue, Saturation, and Lightness) color space representations may also be used. Embodiments then perform a function utilizing a Fast Fourier transform (FFT) algorithm 310 on the at least four vectors of data comprising the color channels and the corresponding vectors after ICA analysis and correction. Results of the Fast Fourier transform provide a series of indicia relative to physiological changes in the body 310. The highest spikes in the series of indicia 312 generally provide for the best usable data for detecting a user's heart rate. However, determining the channel that provides the strongest indicia for detecting the heart rate may comprise a variety of methods such as (1) selecting the signal spike that produces a highest ratio of the peak power over cumulative power, (2) selecting the signal spike where the ratio between the highest spike and a second highest spike is maximized or of greatest magnitude, or (3) reporting the highest signal spike (assumed heart rate) that is produced by the greatest number of channels. Once the channel providing the strongest indicia for detecting the physiological parameter is selected, the physiological parameter may be calculated from the series of indicia, and a biofeedback may be determined and presented to the user 314.

Figure 4:
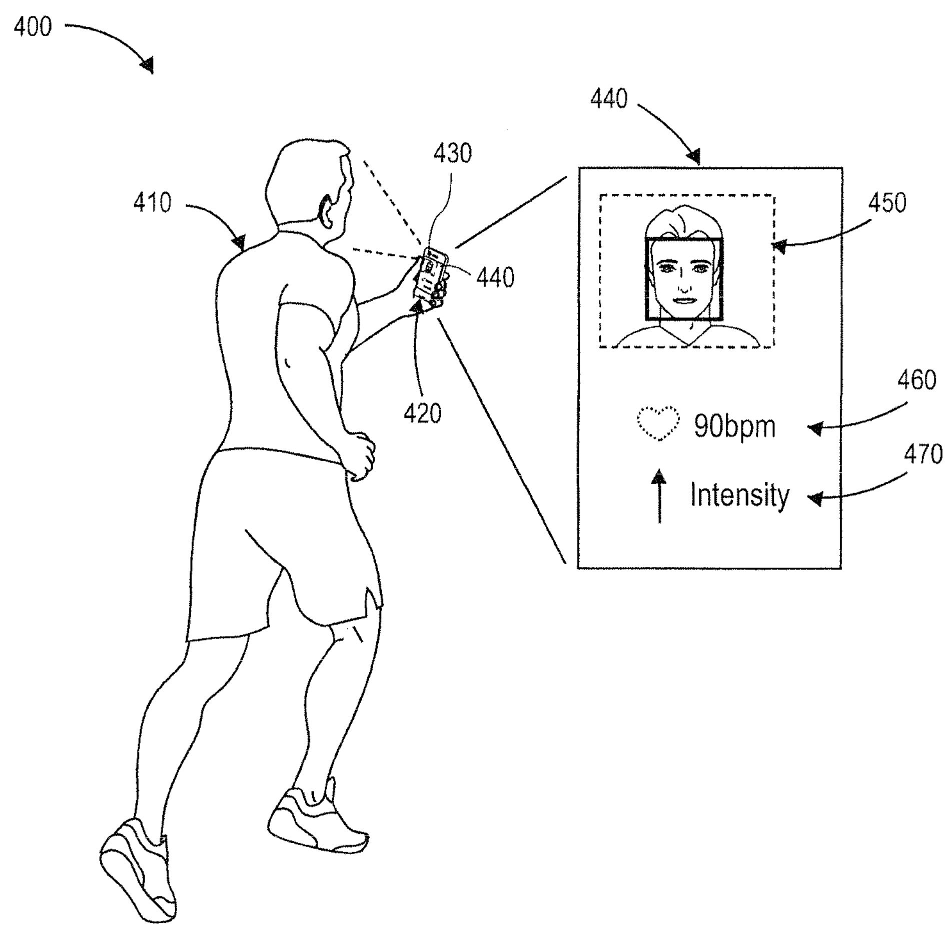
FIG. 4 is a perspective view of a user utilizing an embodiment of the invention.

The invention may involve a computer program for receiving and storing a user's training zone data, or data associated to a detected physiological parameter and utilizing such data to perform cardio assessments for determining the user's training zones. See FIG. 4. Embodiments of the invention 400 may further provide a user 410 with biofeedback 460 during exercise, and provide real-time instructions 470 to the user or an exercise machine for facilitating the user's optimal aerobic intensity. Even further embodiments may provide a user with biofeedback post exercise, in a non-monitoring state, such that a biofeedback is calculated based on a collective record of data over a period of time with purposes of reviewing progression towards predefined goals and/or advising the user on how to further optimize their exercise routine. For example, a series of workouts recorded by the non-invasive biofeedback system may determine the fitness progression of the user based on recorded performance and statistical analysis. The biofeedback system may suggest that a user maintain or increase intensity after a series of successful workout sessions, Another embodiment may simply display to the user a progressive report based on an analysis performed on the series of workout sessions.

While in a biofeedback mode, the computer program of the invention is operable to inform the user 410 if they are above, below, or within their anaerobic threshold 470. Biofeedback indicators 460,470 are generally determined by analyzing the user's current heart rate 460 to the user's heart rate training zone. Heart rate training zones are known in the art to be calculated with a user's maximum heart rate, resting heart rate, and age, or even more accurately determined by performing cardio assessments for the individual user. Resting heart rates are generally a user's heart rate when at rest, when lying down but awake, and not having recently exerted energy. Embodiments of the invention may receive inputs from a user to determine and store a user's personal information necessary for the determination of their training zones. Training zones may be calculated applying a variety of known methods, such as age-adjusted methods, Karvonen formulas, Leger formulas, the Maffetone method, and the Friel method. Further embodiments of the invention may even provide for a cardio assessment mode, wherein the computing device can indicate to a user 410 an instruction to perform a particular behavior or exercise, provide further instruction for measuring the results, ultimately utilizing the results in determination of a user's training zones. Training zones for each user generally have a minimum heart rate value and a maximum heart rate value, such that the range between the minimum and maximum heart rate values determine the optimal range or training zone for the particular user.

The determination of a user's training zones is an initial step to receiving biofeedback from the system. If a user has not set up training zones customized for their individualized use, the biofeedback data will be incomplete, unavailable or inaccurate. Embodiments of the invention may provide for the set-up and storage of user profiles, wherein various users may set up their training zones and training goals for which the biofeedback system may utilize in the customization of biofeedback to the user. Training zones and various intensity levels thereof may be modified by the computer program over any period of time in light of a user's particular training goals. After a user inputs or configures at least their basic training zone values, a user may choose a specific training goal such as weight loss, endurance, increase metabolism, burn fat, physical therapy, strength, etc. It is within the scope of this invention that a user may choose a specific training goal and, based on the chosen training goal, an optimal range is set for the user's training goal based on the user's training zone values.

After the setup of a user's profile, training zones, and/or fitness goals, the user may initiate a biofeedback mode. Upon activation of the biofeedback mode, the embodiments of the computer program will also activate at least a monitoring mode. The monitoring mode is necessary for the provision of biofeedback to a user 410. As the monitoring mode is initiated, the invention will begin the non-invasive detection 430 of the user's heart rate 460 and/or other physiological parameter(s). As data from the monitoring mode is processed in the computing device 420, real-time comparisons are performed to determine the relative position of the user's detected heart rate value to the user's training zone values 470. If a user's detected heart rate 460 is below the optimal range or training zone as determined by the computer program, the computer program will instruct the computing device to present on a display 440, instructions to increase physical intensity 470. On the other hand, if a user's heart rate exceeds their optimal training zone as determined by the computer program, the computer program will instruct the computing device to present on a display 440 instructions to decrease physical intensity. The biofeedback provided in the invention embodies a real-time solution for the optimization of a user's exercise routine in a non-invasive manner.

Figure 5:
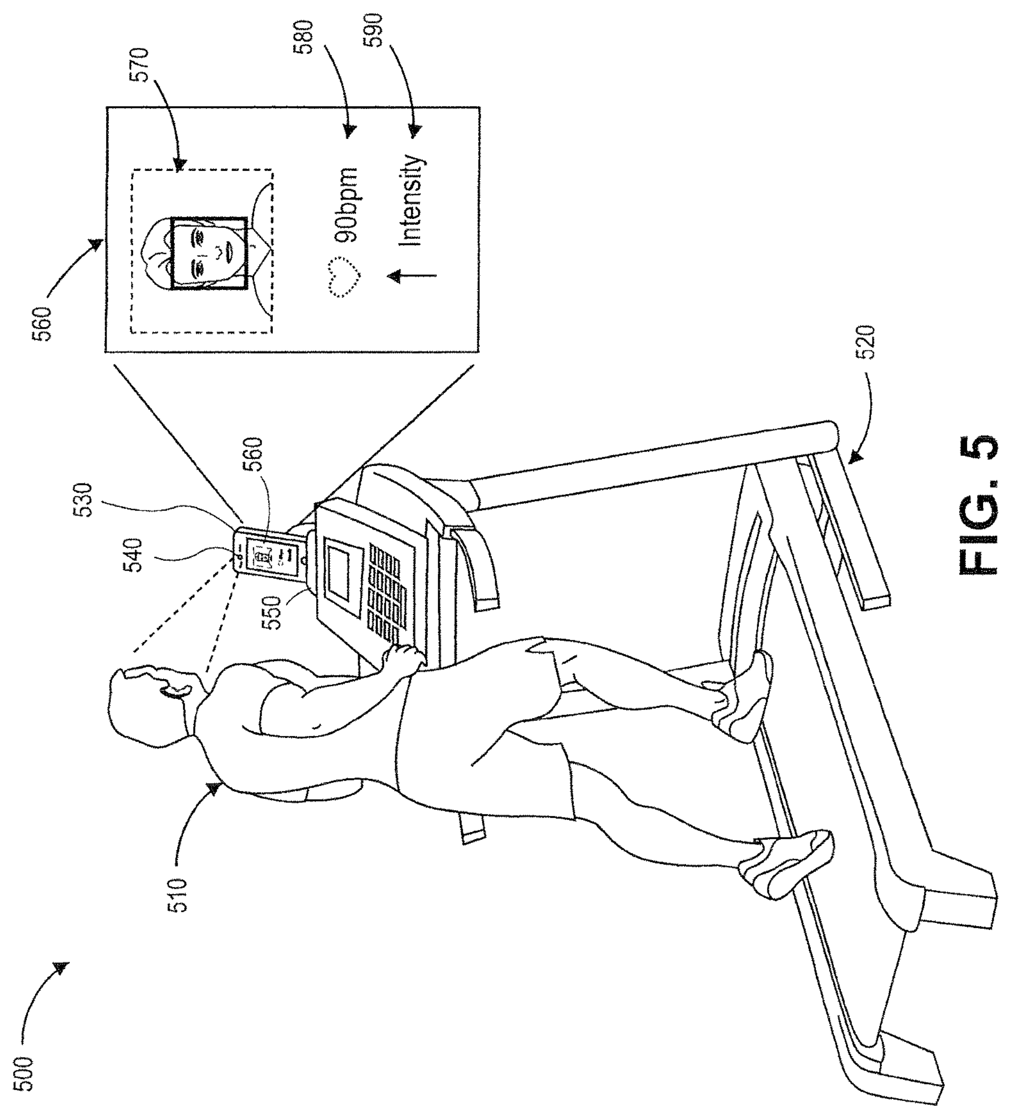
FIG. 5 is a perspective view of a user utilizing another embodiment of the invention.

In even further embodiments of the invention, as illustrated in FIG. 5, the computing device may be operable to detect a user's 510 heart rate while communicating with and controlling an exercise machine 520 (e.g., a treadmill, elliptical machine, cross trainer, stationary bicycle, etc.). In one embodiment of the invention, the computing device and camera(s) may be integrated into the exercise machine itself. Camera(s) built into the exercise machine may calculate the user's physiological parameters and control the machine's intensity/difficulty levels as necessary to keep the user within their desired training zones. Additional embodiments 500 may allow for interfacing between the exercise machine 520 and a user's mobile computing device 530. In one embodiment, the exercise machine 520 may comprise a dock 550 or charging port 550 for the user's mobile device 530, configured so that the mobile device's 530 front-facing camera 540 is oriented towards the user 510 as they exercise on the machine 520. Communications between the mobile device and exercise machine may be enabled through a hardwire connection or via a communications network as described herein. In either the fully integrated or attached mobile device embodiments, the user is provided the option to select a monitoring or biofeedback mode. A third option, the exercise machine control mode, is only available when the invention is in communication with the exercise machine. It is an appreciated aspect of this invention that various safety features such as emergency stops are integrated into the system, including those typically found in modern day exercise machines.

In the event a user's heart rate value is lower than their optimal range or training zone value, the exercise control mode is programmed to send a signal or command to the exercise machine to increase the exercise difficulty either in the form of speed or resistance. Similarly, when a user's heart rate value exceeds their optimal range or training zone value, the computer program sends a signal or command to the exercise machine to decrease speed or resistance. The function embodied in the invention is to accelerate and/or maintain a user's heart rate within the user's desired optimal range or training zone so that the user is optimizing their exercise regimen.

Although the invention has been described with reference to the preferred embodiment(s), it is noted that equivalents may be employed and substitutions made herein without departing from the scope of the invention. Thus, the invention described herein is entitled to those equivalents and substitutions that perform substantially the same function in substantially the same way.

Having thus described various embodiments of the invention, what is claimed as new and desired to be protected by Letters Patent includes the following:

The invention claimed is:

1. A method for non-invasively optimizing a user's exercise routine, the method comprising the steps of:

collecting information about a user for determining said user's optimal range;

tracking a facial area of the user in a live video feed;

detecting a first set of at least two channel values from the facial area of the user in each frame of the live video feed;

making corrective adjustments for user motion and changes in lighting conditions on the first set of at least two channel values, wherein the results of the correction produce a second set of at least two channel values corresponding to the first set of at least two channel values, such that a total of at least four channel values are associated to each frame of the live video feed;

converting each of the at least four channel values associated to each frame of the live video feed into a frequency wave pattern;

selecting a single channel amongst the at least four channel values, wherein the frequency wave pattern of said single channel provides the strongest indicia for physiological parameter detection;

processing the single channel for detecting a physiological parameter; and presenting a biofeedback to the user on a display, wherein the biofeedback notifies the user at least where the detected physiological parameter is relative to the user's optimal range.

2. The method of claim 1, further comprising the step of automatically adjusting intensity levels on an exercise machine such that the user's physiological parameter is brought into the user's optimal range.

3. The method of claim 1, wherein the user's optimal range is a training zone determined by at least the user's minimum heart rate value and the user's maximum heart rate value.

4. The method of claim 1, wherein the facial area tracking step utilizes skin-color detection.

5. The method of claim 1, wherein the facial area tracking step utilizes Haar-like feature detection.

6. The method of claim 1 wherein the physiological parameter is heart rate.

7. The method of claim 1, wherein the corrective adjustment step is an independent component analysis.

8. The method of claim 1, wherein the conversion into a frequency wave pattern step is a Fast Fourier Transformation.

9. The method of claim 1, wherein the selecting of a single channel step selects a frequency spike indicative of a highest ratio of peak power over a cumulative power.

10. The method of claim 1, wherein the selecting of a single channel step selects a frequency spike where a ratio between a highest spike and a second highest spike is maximized.

11. The method of claim 1, wherein the selecting of a single channel step is a most common frequency rate produced by a majority number of channels.

12. The method of claim 1, wherein the video feed is captured utilizing a webcam or mobile device camera.

13. The method of claim 1, further comprising the step of resizing the resolution of video frames for faster processing.

14. A non-transitory computer-readable medium having a computer program stored thereon for execution by a processor, the computer program operable to non-invasively optimize a user's exercise routine, wherein execution of the computer program by the processor performs the steps of:

collecting information about a user for determining said user's optimal range;

tracking a facial area of the user in a live video feed;

detecting a first set of at least two channel values from the facial area of the user in each frame of the live video feed;

making corrective adjustments for user motion and changes in lighting conditions on the first set of at least two channel values, wherein the results of the correction produce a second set of at least two channel values corresponding to the first set of at least two channel values, such that a total of at least four channel values are associated to each frame of the live video feed;

converting each of the at least four channel values associated to each frame of the live video feed into a frequency wave pattern;

selecting a single channel amongst the at least four channel values, wherein the frequency wave pattern of said single channel provides the strongest indicia for physiological parameter detection;

processing the single channel for detecting a physiological parameter; and presenting a biofeedback to the user on a display, wherein the biofeedback notifies the user at least where the detected physiological parameter is relative to the user's optimal range.

15. The non-transitory computer-readable medium of claim 14, further comprising the step of automatically adjusting intensity levels on an exercise machine such that the user's physiological parameter is brought into the optimal range.

16. The non-transitory computer-readable medium of claim 14, wherein the optimal range is a training zone having a minimum heart rate value and maximum heart rate value.

17. The non-transitory computer-readable medium of claim 14, wherein the facial area tracking step utilizes skin-color detection.

18. The non-transitory computer-readable medium of claim 14, wherein the facial area tracking step utilizes Haar-like feature detection.

19. The non-transitory computer-readable medium of claim 14 wherein the physiological parameter is heart rate.

20. The non-transitory computer-readable medium of claim 14, wherein the corrective adjustment step is an independent component analysis.

21. The non-transitory computer-readable medium of claim 14, wherein the conversion into a frequency wave pattern step is a Fast Fourier Transformation.

22. The non-transitory computer-readable medium of claim 14, wherein the selecting of a single channel step selects a frequency spike indicative of a highest ratio of peak power over a cumulative power.

23. The non-transitory computer-readable medium of claim 14, wherein the selecting of a single channel step selects a frequency spike where a ratio between a highest spike and a second highest spike is maximized.

24. The non-transitory computer-readable medium of claim 14, wherein the selecting of a single channel step is a most common frequency rate produced by a majority number of channels.

25. The non-transitory computer-readable medium of claim 14, wherein the video feed is captured utilizing a webcam or mobile device camera.

26. The non-transitory computer-readable medium of claim 14, further comprising the step of resizing the resolution of video frames for faster processing.

27. A system for non-invasively optimizing a user's exercise routine, the system comprising:

at least one video camera mounted in or on a housing and operably connected to a computing module, said at least one video camera oriented towards a user and operable to capture a live video feed of the user;

a computing module with a processor and a memory, said computing module mounted within the housing and configured to:

store optimal range values of a user, wherein the optimal range values are the lower and upper heart rate boundaries defined by a training zone determined by at least a user's resting heart rate and maximum heart rate;

receive the live video feed of the user from the at least one video camera, said live video feed comprising a plurality of frames, said computing module being configured to perform the following actions for each frame:

detect a first set of at least two channel values;

make corrective adjustments for user motion and changes in lighting conditions on the first set of at least two channel values, wherein the results of the corrective adjustments produce a second set of at least two channel values corresponding to the first set of at least two channel values, such that a total of at least four channel values exist;

convert each of the at least four channel values into a frequency wave pattern;

select a single channel amongst the at least four channel values, wherein the frequency wave pattern of said single channel provides the strongest indicia for physiological parameter detection; and process the single channel for detecting a physiological parameter;

a display monitor mounted in or on the housing and configured to display a biofeedback, wherein the biofeedback indicates at least where the physiological parameter of each frame is relative to the optimal range values of the user.

28. The system of claim 27, wherein the housing is a mobile computing device housing.

29. The system of claim 28, wherein the computing module is in communication with an exercise machine and further configured to send data packets to the exercise machine, said data packets corresponding to at least the physiological parameter and the relative position thereof to the optimal range of the user.

30. The system of claim 29, wherein the exercise machine is configured to automatically adjust exercise intensity levels based on the relative position of the physiological parameter to the optimal range of the user.

31. The system of claim 27, wherein the housing is an exercise machine housing.

32. The system of claim 31, wherein the computing module is further configured to automatically adjust exercise intensity levels based on the relative position of the physiological parameter to the optimal range of the user.

33. The method of claim 1, wherein the biofeedback comprises at least one of heart rate, respiration, oxygen saturation, and lactate levels.

34. The non-transitory computer-readable medium of claim 14, wherein the biofeedback comprises at least one of heart rate, respiration, oxygen saturation, and lactate levels.

35. The system of claim 27, wherein the biofeedback comprises at least one of heart rate, respiration, oxygen saturation, and lactate levels.

* * * * *